United States Patent
Lawless et al.

(10) Patent No.: US 7,031,508 B2
(45) Date of Patent: Apr. 18, 2006

(54) REFLECTOMETRY SYSTEM WITH COMPENSATION FOR SPECIMEN HOLDER TOPOGRAPHY AND WITH LOCK-REJECTION OF SYSTEM NOISE

(75) Inventors: John L. Lawless, Pacifica, CA (US); Albert E. Chu, Hillsborough, CA (US)

(73) Assignee: E Y Laboratories, Inc., San Mateo, CA (US)

( * ) Notice: Subject to any disclaimer, the term of this patent is extended or adjusted under 35 U.S.C. 154(b) by 179 days.

(21) Appl. No.: 10/606,010

(22) Filed: Jun. 24, 2003

(65) Prior Publication Data

US 2004/0071331 A1    Apr. 15, 2004

Related U.S. Application Data

(63) Continuation of application No. 09/610,667, filed on Jul. 5, 2000, now Pat. No. 6,584,217, which is a continuation of application No. 09/021,419, filed on Feb. 10, 1998, now abandoned, which is a continuation-in-part of application No. 08/465,089, filed on Jun. 5, 1995, now Pat. No. 5,717,778, and a continuation-in-part of application No. 08/995,590, filed on Dec. 22, 1997, now Pat. No. 6,249,593, which is a continuation of application No. 08/465,089, filed on Jun. 5, 1995, now Pat. No. 5,717,778.

(51) Int. Cl.
*G06K 9/00* (2006.01)

(52) U.S. Cl. .................... 382/133; 377/10
(58) Field of Classification Search ........... 382/132, 382/133, 134, 128, 162, 164, 165, 173, 181, 382/190, 224, 274, 321; 356/39, 335, 246; 435/6, 7.23, 23, 7; 702/20, 21; 422/67, 422/73; 362/572, 575; 436/43, 164, 527, 436/530

See application file for complete search history.

(56) References Cited

U.S. PATENT DOCUMENTS

| | | | |
|---|---|---|---|
| 4,020,151 | A | 4/1977 | Bolz et al. |
| 4,092,068 | A | 5/1978 | Lucas et al. |
| 4,097,845 | A | 6/1978 | Bacus |
| 4,335,427 | A | 6/1982 | Hunt et al. |
| 4,338,024 | A | 7/1982 | Bolz et al. |
| 4,404,289 | A | 9/1983 | Masuda et al. |
| 4,447,153 | A * | 5/1984 | Cremers et al. ............ 356/517 |
| 4,476,231 | A | 10/1984 | Deindoerfer et al. |
| 4,523,853 | A | 6/1985 | Rosenbladt et al. |
| 4,537,861 | A | 8/1985 | Elings et al. |
| 4,538,227 | A | 8/1985 | Toraichi et al. |
| 4,552,458 | A | 11/1985 | Lowne |

(Continued)

FOREIGN PATENT DOCUMENTS

DE    3720166    12/1988

(Continued)

OTHER PUBLICATIONS

McGraw-Hill Encyclopedia of Science and Technology, 1997, 7th Edition, McGraw-Hill, Inc., New York, pp. 411-421.

(Continued)

*Primary Examiner*—Barry Choobin
(74) *Attorney, Agent, or Firm*—Dorsey & Whitney LLP

(57) ABSTRACT

A self-contained system uses light reflectivity to examine intensity of a dyed spot on a device membrane surrounded by background area to discern information about the specimen that produced the spot. In a preferred embodiment, a master clock alternatively drives one LED focussed upon the spot center, and then drives two LEDS focused on the background area. Light reflected from the spot and background is detected by preferably two photodetectors ("PDs") spaced-apart a multiple of 90° azimuthal.

21 Claims, 9 Drawing Sheets

U.S. PATENT DOCUMENTS

| | | |
|---|---|---|
| 4,563,701 A | 1/1986 | Gilath et al. |
| 4,590,582 A | 5/1986 | Umemura |
| 4,611,340 A | 9/1986 | Okazaki |
| 4,647,544 A | 3/1987 | Nicoli et al. |
| 4,648,053 A | 3/1987 | Fridge |
| 4,667,335 A | 5/1987 | Deindoerfer |
| 4,674,108 A | 6/1987 | Asahina et al. |
| 4,676,653 A | 6/1987 | Strohmeier et al. |
| 4,689,670 A | 8/1987 | Okazaki |
| 4,737,464 A | 4/1988 | McConnell et al. |
| 4,755,058 A | 7/1988 | Shaffer |
| 4,769,776 A | 9/1988 | Hiraoka et al. |
| 4,817,123 A | 3/1989 | Sones et al. |
| 4,850,029 A | 7/1989 | Moyer et al. |
| 4,855,930 A | 8/1989 | Chao et al. |
| 4,875,104 A | 10/1989 | Kamon |
| 4,882,492 A | 11/1989 | Schlager |
| 4,884,213 A | 11/1989 | Iwata et al. |
| 4,891,757 A | 1/1990 | Shroy et al. |
| 4,922,915 A | 5/1990 | Arnold et al. |
| 4,983,032 A * | 1/1991 | Van Den Brandt ........... 353/30 |
| 5,008,185 A | 4/1991 | Bacus |
| 5,014,216 A | 5/1991 | Stafford et al. |
| 5,018,209 A | 5/1991 | Bacus |
| 5,028,139 A | 7/1991 | Kramer et al. |
| 5,037,614 A | 8/1991 | Makita et al. |
| 5,039,225 A | 8/1991 | Uekusa |
| 5,046,003 A | 9/1991 | Crawford |
| 5,071,248 A | 12/1991 | Tiefenthaler et al. |
| 5,121,338 A | 6/1992 | Lodder |
| 5,151,966 A | 9/1992 | Brehm et al. |
| 5,159,412 A | 10/1992 | Willenborg et al. |
| 5,189,495 A | 2/1993 | Brunsting et al. |
| 5,218,419 A | 6/1993 | Lipson et al. |
| 5,231,576 A | 7/1993 | Suzuki et al. |
| 5,239,696 A | 8/1993 | Balch et al. |
| 5,279,925 A | 1/1994 | Berger et al. |
| 5,320,814 A | 6/1994 | Walt et al. |
| 5,321,492 A | 6/1994 | Detwiler et al. |
| 5,353,799 A | 10/1994 | Chance |
| 5,413,939 A | 5/1995 | Gustafson et al. |
| 5,437,840 A | 8/1995 | King et al. |
| 5,463,467 A | 10/1995 | Baumann et al. |
| 5,473,706 A | 12/1995 | Bacus et al. |
| 5,485,527 A | 1/1996 | Bacus et al. |
| 5,515,170 A | 5/1996 | Matzinger et al. |
| 5,518,689 A | 5/1996 | Dosmann et al. |
| 5,526,258 A | 6/1996 | Bacus |
| 5,537,374 A | 7/1996 | Wachi |
| 5,604,105 A | 2/1997 | Jackowski |
| 5,616,502 A | 4/1997 | Haugland et al. |
| 5,633,724 A | 5/1997 | King et al. |
| 5,642,192 A | 6/1997 | Gordon et al. |
| 5,654,803 A | 8/1997 | Howard, III et al. |
| 5,661,563 A | 8/1997 | Howard et al. |
| 5,706,094 A | 1/1998 | Maris |
| 5,717,778 A | 2/1998 | Chu et al. |
| 5,738,997 A | 4/1998 | Hayashi et al. |
| 5,781,299 A * | 7/1998 | Womack et al. ............ 356/507 |
| 5,828,776 A | 10/1998 | Lee et al. |
| 5,831,254 A | 11/1998 | Karpen |
| 6,081,325 A | 6/2000 | Leslie et al. |
| 6,118,516 A | 9/2000 | Irie et al. |
| 6,172,744 B1 * | 1/2001 | Scharlack et al. ............ 356/39 |
| 6,248,988 B1 | 6/2001 | Krantz |
| 6,515,292 B1 * | 2/2003 | Scherer et al. ......... 250/492.24 |
| 6,584,217 B1 * | 6/2003 | Lawless et al. ............. 382/133 |
| 6,586,193 B1 * | 7/2003 | Yguerabide et al. ....... 435/7.92 |
| 2002/0061178 A1 * | 5/2002 | Winston et al. ............. 385/133 |
| 2002/0137091 A1 * | 9/2002 | Luttermann et al. ......... 435/7.1 |
| 2003/0157731 A1 * | 8/2003 | Yguerabide et al. ........ 436/523 |
| 2003/0171655 A1 * | 9/2003 | Newman et al. ............ 600/200 |
| 2003/0207328 A1 * | 11/2003 | Yguerabide et al. ......... 435/7.1 |
| 2004/0062028 A1 * | 4/2004 | Winston et al. ................ 362/31 |
| 2004/0246606 A1 * | 12/2004 | Benitez et al. ............. 359/858 |
| 2004/0252390 A1 * | 12/2004 | Benitez et al. ............. 359/858 |
| 2005/0048599 A1 * | 3/2005 | Goldberg et al. ............. 435/34 |
| 2005/0112784 A1 * | 5/2005 | Yguerabide et al. ........ 436/518 |
| 2005/0185178 A1 * | 8/2005 | Gardner et al. ............. 356/301 |

FOREIGN PATENT DOCUMENTS

EP        0 417 551 A2     3/1991

OTHER PUBLICATIONS

McGraw-Hill Yearbook of Science and Technology, 1997, McGraw-Hill, New York.

* cited by examiner

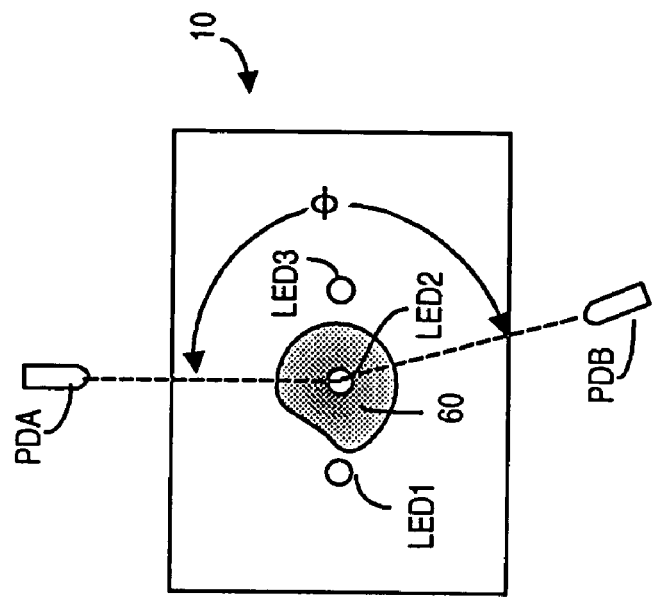
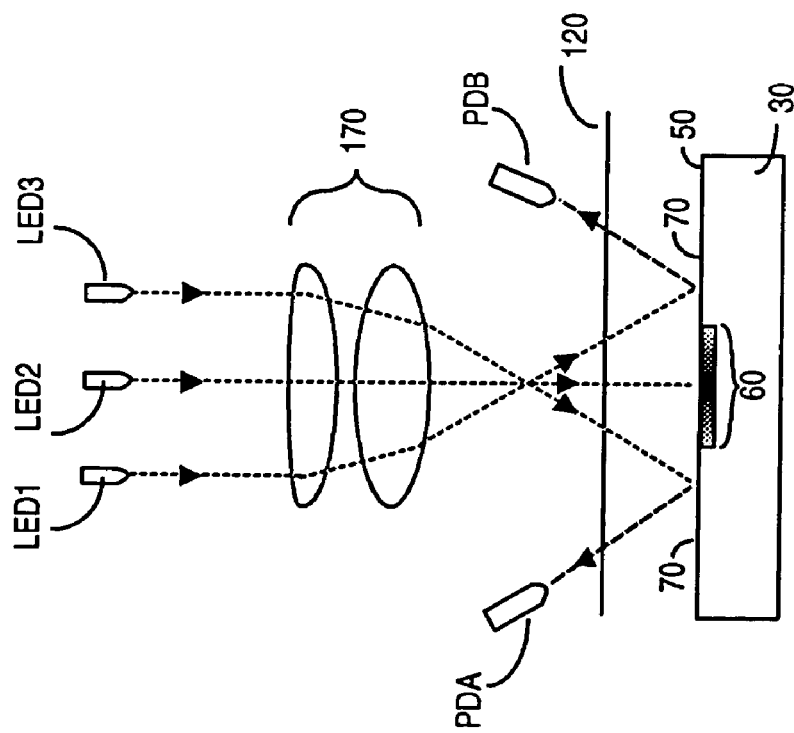
FIG. 4B
FIG. 4A

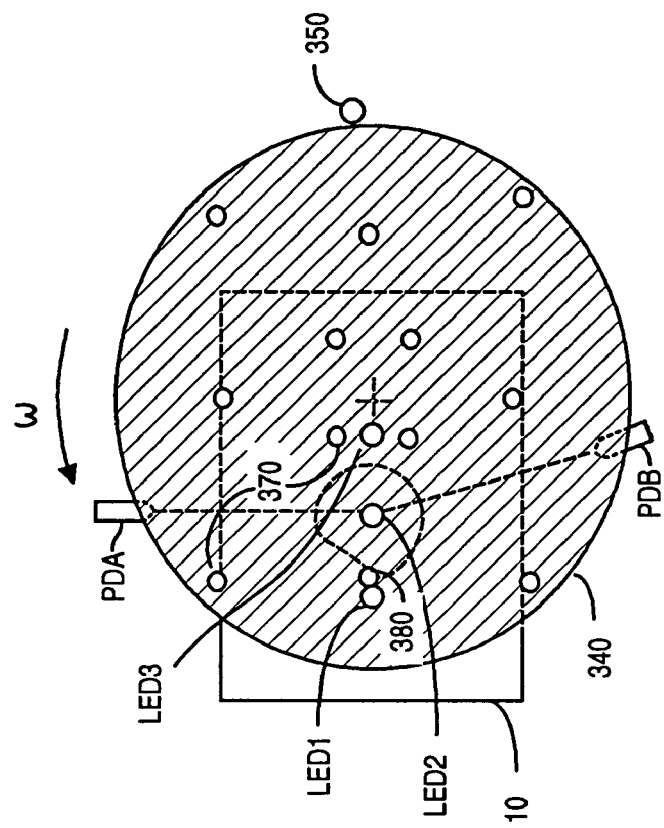
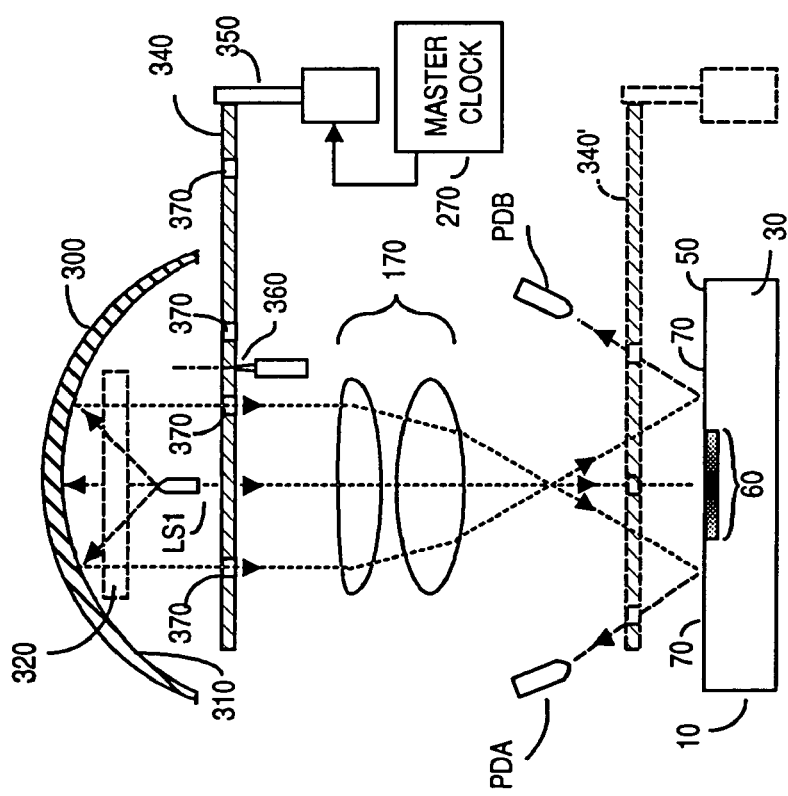
FIG. 7B
FIG. 7A

REFLECTOMETRY SYSTEM WITH COMPENSATION FOR SPECIMEN HOLDER TOPOGRAPHY AND WITH LOCK-REJECTION OF SYSTEM NOISE

RELATIONSHIP TO OTHER PENDING APPLICATIONS

This is a continuation of application Ser. No. 09/610,667 filed Jul. 5, 2000 entitled REFLECTOMETRY SYSTEM WITH COMPENSATION FOR SPECIMEN HOLDER TOPOGRAPHY AND WITH LOCK-REJECTION OF SYSTEM NOISE which will issue as U.S. Pat. No. 6,584,217 on Jun. 24, 2003, which was a continuation of application Ser. No. 09/021,419, filed on Feb. 10, 1998, now abandoned which was a continuation-in-part from application Ser. No. 08/465,089 filed Jun. 5, 1995, entitled OPTICAL SPECIMEN ANALYSIS SYSTEM AND METHOD, which issued as U.S. Pat. No. 5,717,778 on Feb. 10, 1998, and from application Ser. No. 08/995,590 entitled OPTICAL SPECIMEN ANALYSIS SYSTEM AND METHOD, filed on Dec. 22, 1997, a continuation of said Ser. No. 08/465,089. Applicants incorporate each said application herein by reference.

FIELD OF THE INVENTION

The invention relates to reflectometry systems in general, and more particularly to reflectometry systems and methods used to analyze change in a characteristic such as color or optical density of an area of a testing substrate. Such area may include colored spots that can represent a chemical condition in a specimen in a molecular recognition application (among other applications) to discern meaningful information from contrast signals.

BACKGROUND OF THE INVENTION

It is known in the art to analyze biological and other specimens using optical techniques, including automatic optical analysis systems. Often it is desired to detect the presence of a particular analyte potentially within a specimen by testing for a reaction of the analyte with a specific reagent that can bind to the analyte. Such molecular recognition reactions represent the complexing of molecules that possess a high binding affinity to each other.

For example, consider the detection of the analyte human chorionic gonadotropin (HCG), a hormone present in the urine of pregnant women, as an indication of pregnancy. A few drops of urine are exposed to a substrate having a reagent thereon that is known to bind to HCG. In performing such testing, additional reagents may be added to the testing substrate such that a change in characteristic (e.g., color) in at least a portion of the results if HCG is present in the urine. The resultant color change can be clearly visible to the untrained eye and can serve as a home pregnancy test.

At best, the human eye can give qualitative results. But often tests do not produce readily ascertainable "yes" or "no" results that are unambiguously apparent, even for a laboratory technician who is experienced in performing the tests and reading the results. Also, for some tests, quantitative results are desired, for example the measurement of progression or extent of a disease state. Visual examination of color and contrast changes are only qualitative and the eyes of one observer will have a different sensitivity than the eyes of another observer. Even if two observers with identical visual sensitivity could be found, fatigue and subjective judgment differences could provide different results for identical data.

Many other molecular recognition applications, both immunological and non-immunological, can provide a meaningful contrast signal that can be analyzed using contrast data. In addition to immunological pair applications (e.g., antibody-antigen "Ab-Ag"), various sandwich format matrix assay techniques such as Ab/Ag/Ab, or Ag/Ab/Protein A-gold can generate meaningful contrast signals, as can bindings between avidin-biotin derivatives, or lectin-carbohydrate binding. Many applications use hormone receptors as molecular recognition sites, and reaction specific binding is a powerful analytical tool used in DNA hybridization. Such applications would benefit if more reliable and automated analytical tools could be provided.

Various systems have been attempted to provide an automated reliable system for analyzing results obtained from immunological and non-immunological molecular recognition applications. In some tests, especially those involving immunoassay devices, it is necessary to discern the presence and reflectivity of dye-colored spots relative to the background area surrounding the spot. For example, when testing electrophoretic immunoblots ("Western Blots") a densitometer is used to measure optical density of light reflected from nitrocellulose strips. But color density of antibody-produced color bands in the strips can vary, as can the background color. As a further complication, densitometers used in such tests cannot measure more than a single point in a color band. Thus, while densitometry can produce automated results, the results may vary greatly and can be highly inaccurate.

U.S. Pat. No. 5,006,464 to Chu et al. discloses the use of reflectometry to more rapidly quantitate the results of immunoassay tests. Suppose, for example, it is desired to examine human blood using such rapid immunoassay testing. A few drops of a blood, serum, or plasma specimen are deposited onto a testing substrate of an analytical device. The testing substrate is oftentimes a porous membrane that has one or more receptor chemicals bound thereon at discrete areas of the membrane that bindingly react to one or more target analytes, if present within the blood. Typically, after addition of the blood specimen, a few drops of a labeled reagent that may include a colored dye are added to the testing substrate. Finally, a few drops of a washing solution may be added to the testing substrate to remove any residual reagents that have not specifically bound to the discrete areas of the membrane where the receptor chemicals are located. The presence of the target analyte in the blood may then be indicated by the presence of a dye-colored spot on the device, relative to the uncolored surrounding background (which will be the area of the testing substrate that does not have receptor chemicals bound thereon). Such testing of course is not limited to the diagnosis of a particular analyte within blood, but may also be carried out with other types of specimens, biological or otherwise, that may contain target analytes of interest.

FIG. 1A depicts an exemplary device 10 that may be used to carry out the above-described Chu type analysis. Device 10 may measure perhaps 1 cm square and, for reasons of economy, is fabricated from several layers of cardboard (or sometimes plastic) including upper and lower layers 20, 30. Upper layer 20 defines an opening 40, perhaps 8 mm in diameter, that exposes a surface 50 that lies higher than bottom layer 30. Surface 50 defines a membrane (or substrate) whose preferably porous surface contains at least one immobilized receptor chemical that will cause a binding reaction with a target analyte, when present in a specimen.

FIG. 1B, is a top-view of the device depicted in FIG. 1A, after the above-described testing procedure has been carried out. Spot 60, where a receptor chemical is adhered onto the testing substrate, is shown as being rather (ideally) circular and having a color that is in sharp contrast to the surrounding upper surface 70 of device 10, indicating that the analyte of interest was present in the specimen tested. The challenge is to determine reflectivity of spot 60 relative to surrounding region 70. Stated differently, the challenge is to distinguish between signal from spot 60 and a background reference level from region 70. It will be appreciated that a small change in either signal can result in a substantial change in the difference between the two signals.

The ability to differentiate reflectivity signal from the background reference level permits one to arrive at a meaningful conclusion as to the presence or absence of the target analyte in the specimen. For example, FIG. 1C shows device 10 with no spot whatsoever, e.g., no binding reaction has occurred, and the target analyte is absent from the specimen. In FIG. 1D, a dark spot is present, but as may often be the case, the spot is not uniform in shape and may be smaller in size than anticipated. Spot size can be affected by the area of membrane 50 that was originally impregnated or otherwise treated with chemicals before the specimen was introduced. FIG. 1E depicts a uniform spot 60, but of less opaqueness than the spot shown in FIG. 1B, while FIG. 1F shows a non-uniformly shaped spot of less opaqueness than was shown in FIG. 1A or FIG. 1C.

It can be rather difficult to accurately discern reflectivity of spot 60 relative to the surrounding region 70. This is especially true if distinguishing signal from noise is to be accomplished rapidly, preferably in an automated fashion, without requiring trained personnel. In many applications, the difference between a positive reading and a negative reading can be less than about a ±1% change in reflectivity. In practice, borderline readings often occur when spot reflectivity is perhaps 98% of background reflectivity. In practice, a reading of 98.4% would be negative, while a reading of 97.6% would be positive. Thus, it is important that reflectivity be interpreted accurately and consistently if meaningful data are to be obtained. Even a trained human eye cannot resolve changes in reflectivity as small as a few percent. The human eye is also a poor reflectometry instrument when one must examine many devices 10 within a given time. Fatigue, subjective differences in observation, and errors can result in different analysis results, even when reflectivity changes are large enough to permit differentiation with the eye.

Accordingly, an automated system for correctly ascertaining reflectivity data is required. Typically after exposure to a specimen, and post-exposure treatment and dyeing as described above, device 10 is inserted into a reflectometry device. A reflectometer subjects at least the spot area of the device to light, and attempts to measure intensity of light reflected from the spot area (the signal) and from representative surrounding region (the reference signal). But unless the device is inserted into the reflectometer in an aligned manner, light from the receptor spot area may not be accurately measured. Indeed, for low density spots, it can be difficult to discern dot intensity from background area intensity. The colored spot itself may not be uniformly colored, and the spot signal reading may be highly dependent upon what portion of the receptor area spot was examined for reflected light intensity.

Further, conventional reflectometer signal processing units tend to be relatively large and cost upwards of $1,500 per unit to manufacture, exclusive of a signal processing computer, typically requiring at least a 80486-type microprocessor. For example, charge control device ("CCDs") not unlike what is found in modern video cameras were often used to try to measure intensity. However pixel-to-pixel sensitivity variations in such devices made calibration and consistent data readings somewhat difficult. Further, in addition to bulk and expense, such systems were not especially robust mechanically.

Even if the above problems did not exist, the surface of membrane 50 commonly provides an irregular surface topography. This irregularity is present with inexpensively produced devices containing cardboard or paper membrane surfaces, as well as with higher quality woven cloth surfaces. As used herein, the term membrane is understood to include paper, cardboard, cloth, and other commonly used membrane materials used in producing a device 10. Although optical-quality membranes (e.g., glass, ceramic, metal) would present a substantially planar surface, these more expensive materials are not suitable to hold the desired chemicals, while allowing for diffusion of water and the like.

As a result, even if color intensity in the receptor area were somehow completely uniform and very discernable from the background region, irregularities in the membrane surface would still introduce error into the intensity readings. Although for immunoassay tests in which a high intensity spot results, a 1%–2% intensity readout error might be acceptable, for other tests an error of 1% or 2% may result in a completely false result.

What is needed is a technique for rapidly and accurately analyzing intensity signals produced by spots on devices, where spot density contains important data. Such technique should be applicable for immunological and non-immunological molecular recognition applications. Such technique should exhibit improved signal to noise characteristics, and preferably should compensate for irregularities in the device topology. The technique should be mechanically robust, simple enough for a layman to operate, and should be relatively inexpensive to produce and maintain.

The present invention provides such a method and a system for carrying out the method.

SUMMARY OF THE PRESENT INVENTION

The present invention provides a self-contained system that examines a device containing a membrane upon which is formed a dyed spot surrounded by undyed background. The dyed spot may be the result of molecular recognition, including immunologically and non-immunologically based applications, among other applications. The invention uses light reflectivity to determine relative spot signal to background reference signal, to glean meaningful and information as to spot intensity. This information allows quantifying a target analyte or chemical or substance, whose presence contributed to the spot dye characteristic.

The membrane surface will include a spot dyed region that is responsive to the presence of the target substance, which spot region is typically surrounded by an undyed background region. In a preferred embodiment, the present invention alternatively illuminates the spot region and the background region, and measures intensity of light reflected from each region. In another embodiment, the membrane surface is illuminated (dyed spot region and background region) and then the spot region or the background region but not the spot region is illuminated. The intensity of light reflected during the various modes of illumination may be subtracted to cancel the zero output drift effects associated with amplified signals from the light detectors in the absence of light. The emitter light may come from preferably three substantially identical light sources, e.g., light emitting diodes ("LEDs"), one of which is aimed at the spot region and two of which air aimed at the background regions. A master clock unit actively drives the LEDs to alternately illuminate the spot and the background. Alternatively, the master clock unit can cause the LEDs to simultaneously illuminate spot and background regions, alternating with time periods during which only the spot or only the background without the spot is periodically illuminated. Other embodiments provide a single light source, whose light output is directed uniformly upon spot and background regions, for example using a diffusive or reflective reflector unit. In such embodiment, control over what device surface regions receive light is controlled by a master clock unit controlled perforated rotating mechanical shutter, or by a solid state preferably liquid crystal shutter. In the various embodiments, the light source(s) define one plane and the membrane containing the spot and background regions define a second plane. The light source(s) may be disposed at either plane, and the light detectors disposed at the remaining plane. The emitted light spectra may be visible, invisible, infrared, ultra-violet, X-ray, and may be produced from a variety of sources including LEDs, laser diodes, incandescent lights, among other light sources.

The reflected light, which is to say a fraction of the emitted light, is then detected preferably by photodetectors ("PDs") spaced-apart a chosen multiple of 90° azimuthally. Depending upon the topology of the device membrane surface, there preferably will be two PDs that are azimuthally spaced-apart 180° or 90°.

The invention provides two sub-systems: a sub-system that substantially reduces skew error due to uneven device topography, and a phase lock-in amplifier sub-system to enhance detected signal/noise by measuring signal voltage without producing noise.

In the first sub-system, the present invention recognizes that poor topography associated with commonly used membranes can contribute an uncertainty error of at least ±1% in reflected light intensity readings. This error, which is approximately sinusoidal, is substantially cancelled by monitoring reflected light intensity using two PDs spaced-apart from each other 180° azimuthally. Should a membrane be fabricated from cross-linked cardboard, then the two PDs are spaced-apart from each other 90° azimuthally. So disposing a pair of PDs a chosen multiple of 90° azimuthally apart, and averaging their output signals can improve accuracy ±1% or more.

In the second sub-system, the averaged PD output signal is simultaneously positively and negatively amplified, and the positive and negative amplified signals are sampled with a switch that operates synchronously with the active region of the LED drive signals. The result is that only in-phase signals occurring during the active LED drive signal portion can be sampled. Further, signals that are present at the output of the PD summing amplifier are essentially doubled in effective amplitude, thereby enhancing signal/noise ratios.

The output of the switch is coupled to a lowpass filter that attenuates frequencies higher than the measurement frequency, perhaps 3 Hz. The measurement frequency is substantially lower than the LED clock switching frequency. As such, the lowpass filter output is substantially free of noise, other than noise components within a few Hz of the clock frequency. The lowpass filter thus recovers a signal proportional to spot light intensity, and exhibits excellent signal to noise characteristics.

Other features and advantages of the invention will appear from the following description in which the preferred embodiments have been set forth in detail, in conjunction with the accompanying drawings.

BRIEF DESCRIPTION OF THE DRAWINGS

FIG. 4A is a side view of a preferred configuration for monitoring intensity of reflected light such that skew due to membrane topography is minimized, according to the present invention;

FIG. 4B is a simplified plan view of the configuration shown in FIG. 4A, to depict azimuthal angular orientation between photodetectors, according to the present invention;

FIG. 7A is a side view of an alternative embodiment in which a single light source and a rotatable mechanical shutter are used to minimize skew due to membrane topography, according to the present invention;

FIG. 7B is a simplified plan view of the configuration shown in FIG. 7A, according to the present invention;

DETAILED DESCRIPTION OF THE PREFERRED EMBODIMENT

Figure 2:
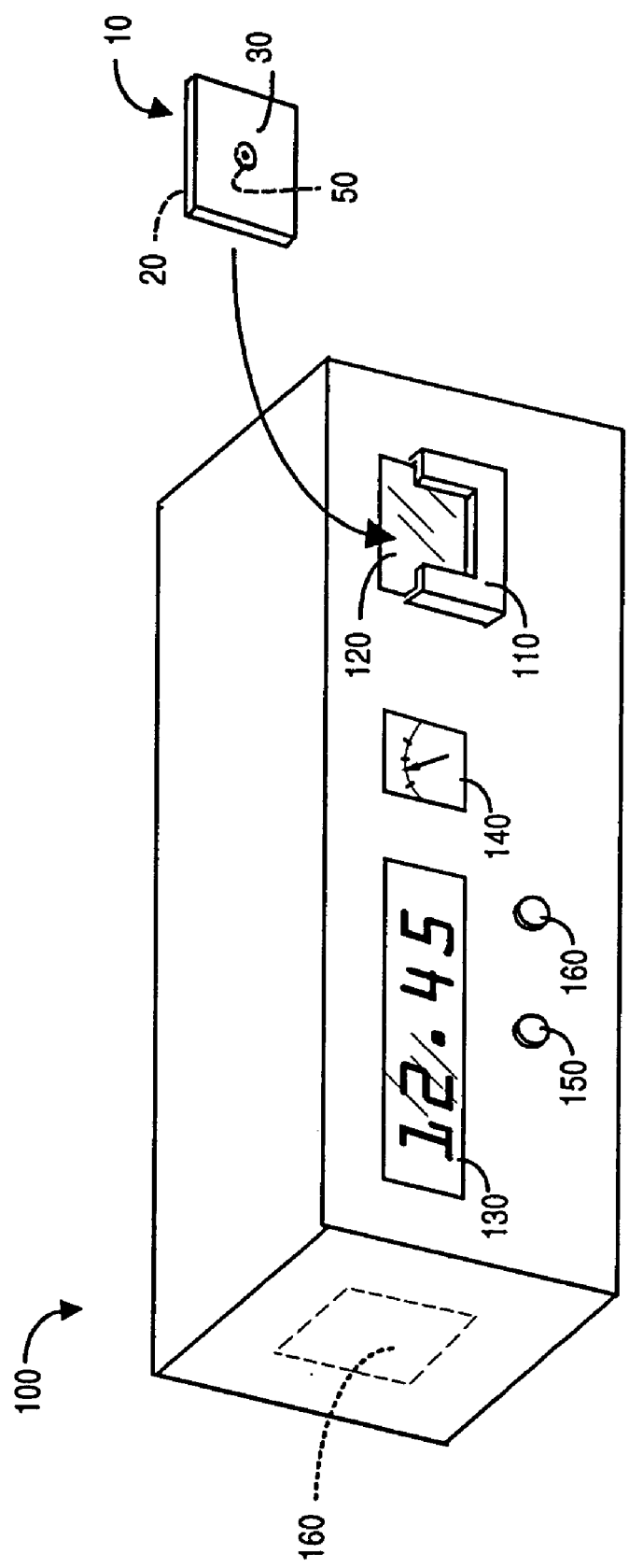
FIG. 2 is a perspective view of the present invention.

FIG. 2 is a perspective view of the present invention, a reflectometer system 100 with compensation for specimen holder topography and with lock-rejection of system noise.

The housing for system 100 includes a device holder 110 that is mounted adjacent a window 120 that is substantially transparent to light generated within system 100. Holder 110 is sized to retain a device 10 such as described earlier herein. Device 10 is inserted into holder 110 with the chemically dyed spot facing window 120. (As used herein, the term dyed spot refers generically to a characteristic change in region 60, for example, any change in contrast, in color, color or optical density, without limitation.)

Thus, surface 20 of device 10 faces system 100, and opposite surface 30 faces away from system 10. In a preferred embodiment, system 100 includes a visual readout device, preferably a digital readout 130 and/or an analog readout device 140. Of course readout device 130 and/or 140 could be replaced or augmented with at least one light emitting diode ("LED") biased to turn-on or turn-off or change color if an acceptable intensity value is measured from a spot 50 on device 10. System 100 typically will includes one or more controls 150, 160, for example to turn the system on or off, or to provide a manual calibration function if desired.

For purposes of the present invention, system 100 is intended to quantize relative reflectivity between a spot 60 and a background 70, for example as shown in FIGS. 1A, 1C–1F. In a biological test application, spot 60 will have been produced by subjecting an analyte to chemicals, including chemicals present in membrane 50 (see FIG. 1A) before introduction of the analyte. However as a practical matter, the present invention can provide an accurate measure of relative reflectivity substantially independently of how spot 60 is formed. For example, it may be desirable to use system 100 to analyze paint samples, presented as spots 60 on a membrane 50 on a device 10.

As noted, membrane 50 typically is cardboard, a relatively inexpensive material, but unfortunately a material characterized by a somewhat rough topography. Applicant has discovered that the topography common with cardboard used to fabricate membrane 50 in devices 10 can easily contribute at least a ±2% error in the measured intensity of reflected signals. Unfortunately, in many applications, especially biomedical applications, a ±2% error can spell the difference between a true reading and a false negative or false positive reading.

Figure 3B:
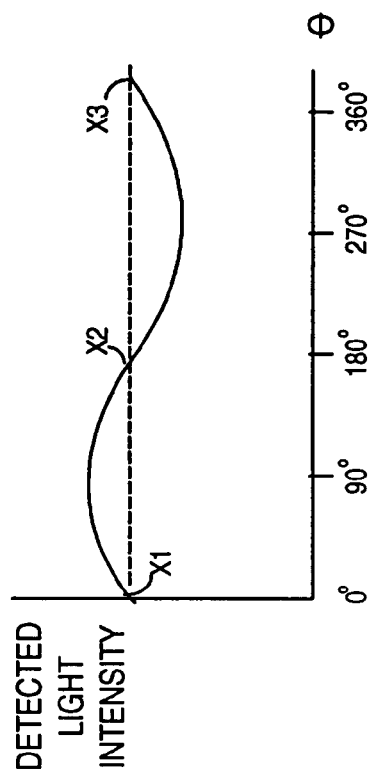
FIG. 3B depicts a trigonometric relationship discovered by applicant between intensity of reflected light, and angular orientation between light detectors, according to the present invention.
Figure 3A:
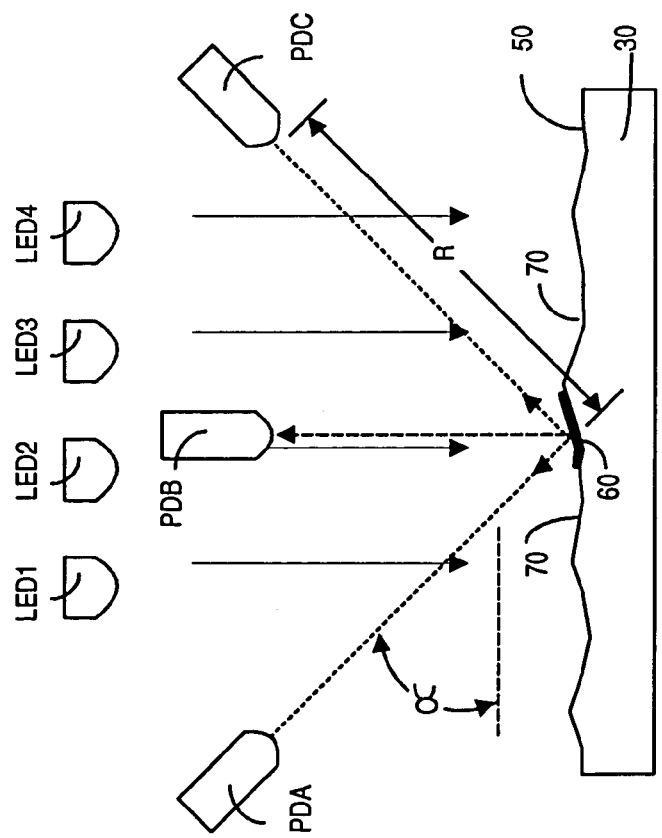
FIG. 3A depicts a conventional configuration for monitoring intensity of reflected light, according to the prior art.

FIG. 3A and 3B are helpful in understanding the nature of the topography problem and the solution discovered by applicant. FIG. 3A shows in exaggerated form the mountain-like topography of the upper surface of membrane 50. FIG. 3A also depicts two of the three parameters used to identify a point in spherical coordinates, namely altitude angle α, and radius R; the third parameter, an azimuthal angle Θ would be seen in a plan view.

In FIG. 3A, a rather dark spot 60 is shown on membrane 50 as well as background portions 70. Assume that reflectivity was to be measured by shining collimate light onto membrane 50, for example from a plurality of light emitting diodes denoted LED1, LED2, . . . LED4, although fewer or more than four LEDs might be used. The intensity of light reflected from spot 60 and from background 70 is often detected with a plurality of light detectors, here shown as photodiodes, PDA, PDB, and PDC, although other photodetectors could be used, e.g., photo-multiplier tubes.

If the upper surface of membrane 50 were perfectly planar, it is evident that light would be reflected uniformly from background portions 70, and that light would be reflected less intensely but ideally uniformly from spot 60, assuming the spot were uniform in color density. But planar membrane surfaces are expensive to produce, and what is shown in FIG. 3A is a closer approximation to what is encountered with actual devices 10 made from cardboard. Because spot 60 is slanted, due to the poor membrane topography, it is evident that PDA will receive more reflected light signals than will PDC. On a macroscopic scale, PDA sees a larger projected area from spot 60 than is seen from the perspective of PDC. As a result, PDA will receive signals whose intensity ideally will show a sharp contrast as the perimeter of spot 60 is viewed.

The skewing in intensity of reflected light signals has simply been tolerated in the prior art, with the result that a relatively large uncertainty error has come to be accepted. However, applicant has discovered that there is a sinusoidal transfer function associated with the uneven topography that has been described, and that if two photodetectors that are placed 180° apart from each other are used, intensity skew error due to membrane topography can be improved by at least about ±1%. (Intensity variations of ±1% or so are simply not visible to the unaided eye.)

It is also noted that topography effects exist from device-to-device, and indeed for a single device as a function of time, for example as the spot continues to dry out, or the membrane surface will change in response to ambient temperature and/or humidity. Further, the color of the nominally white, undyed membrane regions 70 may in fact be other than white, and may vary from device-to-device, and indeed over different regions of a single device.

Although a 1% or 2% improvement in skew error correction does not sound significant, in practice it can made the difference between good results and questionable results, especially when faint contrast spots are to be read. It is precisely when such questionable spots, which normally are characterized by poor signal/noise ratio, are to be analyzed that the highest possible measurement accuracy is most needed. Understandably, in a medical testing environment, a false reading from a system such as system 100 can have serious ramifications for the subject from whom the analyte specimen under test was taken.

FIG. 3B, depicts the intensity of reflected light measured by a light detector (e.g., PDA) as azimuthal (or longitudinal) angle Θ is varied. As used herein, Θ defines the angle of a cone whose axis of symmetry is orthogonal to the nominal membrane plane, wherein the photodetectors are disposed on the surface of the cone, spaced-apart the angle Θ.

Note in FIG. 3B that if intensity measurements are taken precisely Θ=180° apart, e.g., data point X1 and data point X2, or data point X2 and data point X3, that a constant light intensity value is obtained, independently of the topography variation contribution. Stated differently, if intensity of reflected light is obtained using only two photodetectors that are spaced Θ=180° apart, the summation (average) signal from the two photodetector outputs will substantially cancel the topography sinusoidal variation. This result follows from the relationship $\{\sin(\Theta) + \sin(\Theta + 180°)\} = 0$.

The type of cardboard membrane 50 that produces the sinusoidal topography function may have non-linked or parallel grain in the paper. Applicant has discovered that for a different type of cardboard membrane, apparently a cross-grained paper, the frequency shown in FIG. 3B doubles, e.g., data measurements made not 180° apart but rather 90° apart substantially nullify topography error. Understandably the topography cancellation is not perfect because the relationship shown in FIG. 3B is not a perfect sinusoid, but is a good approximation.

In the embodiments of FIGS. 3A and 3B, two optical planes are present: a plane at the source of the emitted light, and a plane at the substrate. If desired, the roles of the LEDs and PDs may be reversed, by replacing LEDs 1, 2 and 3 with PDs 1, 2, 3 and replacing PDA and PDB with LED1 and LED2, preferably mounted at 180° azimuthally to reduce topography errors. In this embodiment, all of the specimen may be simultaneously illuminated by LED1 and LED2, which preferably are flashed on and off in response to driver signals commanded by the master clock unit. In this embodiment, the signals from PD1, PD3 (focussed on the background region) and signals from PD2 (disposed above and focussed on the spot) may be subtracted to cancel drift errors.

FIG. 4A shows a top view of a preferred implementation of the above-described findings, while FIG. 4B is a simplified plan view, in which the azimuthal angle Θ is seen. In FIG. 4A, three light sources LED1, LED2, LED3, and only two light photodetectors (PDs) PDA and PDB are used.

It is desired to observe relatively subtle changes in reflectivity between the spot and representative surrounding membrane regions, taking into account topography imperfections. In the present invention, the number of light sources was limited to three to maximize cancellation of the sinusoidal variations in intensity described earlier herein. In the preferred configuration, a line through the membrane regions illuminated by the three LEDs (PDA, PDB, PDC) is perpendicular to a line between the receptor PDs, as projected onto the membrane. The three light sources permits attaining a reading from the spot per se (e.g., the desired signal), and two representative surrounding background regions (which provide a background reference area signal), while obtaining the topography-cancellation benefits noted.

LED1, LED2, LED3 are all mounted on a line or first plane that is parallel to the nominal, ideally flat or second plane of the membrane. The distances between the LEDs and the membrane plane will vary somewhat, as a function of the focal length of the lens system, which length varies between on-axis LED2 and off-axis LED1, LED2. The spaced-apart distance between adjacent LEDs is about 6.3 mm, and is determined by the nominal size of the spot (typically about 1.6 mm) and by the magnification of the optical system. If nominal spot size were increased, then it would be desired to also increase the spaced-apart LED distances.

The central region of the spot will be associated with low reflectivity that extends radially outward with increasing reflectivity until eventually the non-dyed background portion 70 of the membrane is encountered. In practice there is a transition from spot to background. LED2 is intended to focus light primarily upon the center of the spot, whereas LED1 and LED2 are intended to focus light upon the background periphery region.

The LED-emitted light is primarily diffusely reflected. The two PDs spaced-apart Θ=180° (preferably within about ±5° or so) provide good intensity readings with the advantage of topography skew cancellation, as noted earlier. As shown in FIG. 4A, ideally photodetectors PDA, PDB are normal to incoming rays of light. PDA and PDB are disposed on a plane equidistance from the nominal plane of the membrane with equal angles of altitude α. Ideally, altitude angle α would be close to 90° to maximize light reception, but in practice α≈30° due to the presence of an optical system 170. Intensity of light received by the photodetectors varies as $$\frac{\sin(\alpha)}{R^2}$$

it is seen that the radial distance R between the target spot and the photodetectors or the LEDs should be small, and equal for each PD. But since each LED is substantially equidistant from the plane of the photodetectors, PDA and PDB each see the same distance-squared intensity effects.

Thus, for use with cardboard membranes of the type producing the characteristic sinusoidal intensity function shown in FIG. 3B, PDA and PDB are spaced-apart 180°, to nullify the skew otherwise measured due to topography irregularities. Of course, instead of using two closely matched, preferably identical detectors PDA, PDB, a single detector PDA could be used, and mechanically moved 180° between measurements. While such an arrangement would ensure that all intensity measurements were made with an identical (e.g., the very same) photodetector, providing a moving mechanical arm or the like would contribute to the cost, bulk, and loss of robustness of the overall system.

If membrane 50 were fabricated from cardboard that evidenced an intensity function of twice the frequency shown in FIG. 3B, then PDA and PDB would be spaced-apart 90°, e.g., would be located on the surface of an imaginary cone whose inner angle was 90°, and whose axis of symmetry were normal to the nominal (ideal) plane of membrane 50.

In FIG. 4A, the three LEDs are focused down on the surface of device 10 by a lens system 170 that preferably includes a plano convex lens and a dual convex lens. The effective focal length is about 1 cm, which an effective high f-stop for good field of focus upon the membrane surface and the spot. Typically the present invention is used to measure intensity for red-dyed spots, but other colored spots should produce good data as well.

LED1, LED2, and LED3 are commercially available high intensity, high brightness 5 mm diameter units, which presently cost perhaps $10/unit. The LED cases include internal, built-in, lens that focus to a divergence angle of about 10°. In practical applications, the nominal size of spot 60 will be known, along with a spot size tolerance. For example, an ideal spot might be 1.6 mm diameter, but in practice sizes may vary from about 1.6 mm to 2.4 mm, with provides that can vary from circular to crescent in shape. (A substantial factor in the spot size is the size and pattern of the chemicals impregnated into the membrane.)

Optical system 160 together with the internal LED lens was designed to make a standard LED focus down to a nominal 1.6 mm diameter. In the preferred embodiment, the effective optical magnification is about 0.34, which is to say the ratio between a 5 mm LED diameter and a nominal 1.5 mm circular spot. Of course other illuminating devices and other focusing systems could instead be used.

Figure 5:
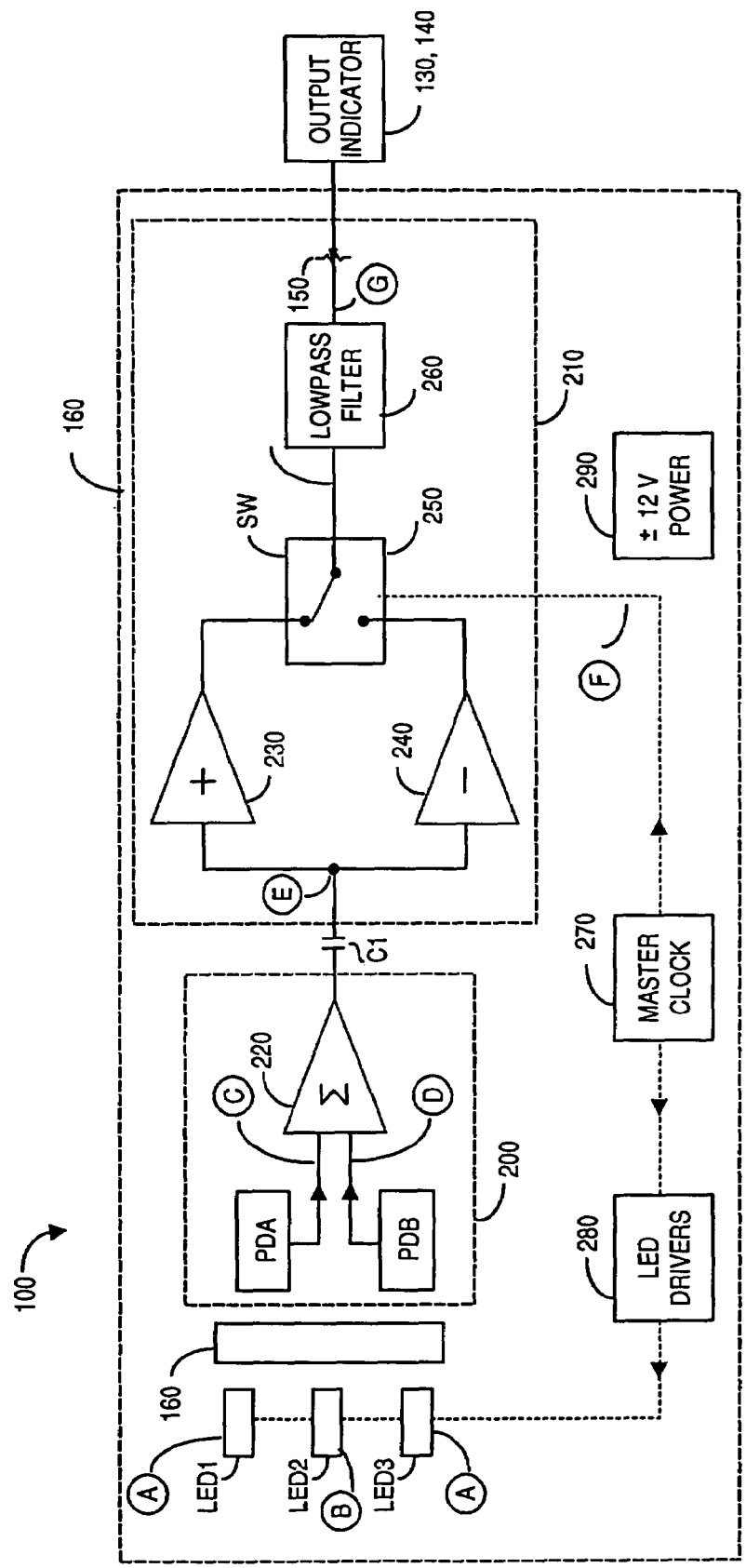
FIG. 5 is a block diagram of a preferred implementation of the present invention.

FIG. 5 is a block diagram of system 100, showing a preferred implementation of circuitry 160. Circuitry 160 includes two important sub-systems: topography skew error reduction sub-system 200, and a lock-in amplifier that enhances detected signal/noise by measuring signal voltage without producing noise. Even if topography compensation sub-system 200 were not present, sub-system 210 would still increase the reliability of obtaining a good known (spot) signal and a good known (background region) reference signal, without receiving excess noise signal at the transition between spot and ambient background.

Figure 6A:
FIG. 6A–FIG. 6G depict waveforms at nodes indicated in FIG. 5.
Figure 6B:

Much of topography skew error reductions sub-system 200 has been described. Two light detectors PDA, PDB are spaced-apart $\Theta=180°$ (or $\Theta=90°$ if a device 10 uses a cross-grained type paper membrane), and their outputs are combined in a summing amplifier 220. As noted, the output of amplifier 220 will be a waveform C that is the averaged sum of the output signals from PDA (waveform A) and PDB (waveform B). These, and other, waveforms are shown in FIG. 6 wherein FIG. 6A denotes waveform A, FIG. 6B denotes waveform B, and so on. FIG. 6D, however, denotes the average sum of waveforms C and D, shown superimposed in FIG. 6C.

In the preferred embodiment, LEDs 1 and 3 are directed at the background or surrounding region 70 on device 10, while LED 2 is directed at the spot 60. In the a preferred embodiment, LEDs 1 and 3 are simultaneously activated by waveform A (shown in FIG. 6A) and LED 2 is activated by a complementary waveform B. The repetition rate and duty cycle of the LED-drive signals are preferably dictated by master clock 270. In the preferred embodiment, these waveforms are square-waves with a repetition frequency of 2 KHz. This frequency was selected because electronic noise including photodiode and operational amplifier system noise is especially low at about 2 KHz. Master clock 270 and driver unit 280 turns-on the center LED2 for about 250 μs, and then turns-on adjacent LED1 and LED3 for about 250 μs, all of the LEDs being driven at the basic clock rate of about 2 KHz. Other drive configurations may also be used. For example, all three LEDs might be turned on simultaneously to illuminate the entire device 10, and in alternate master clock cycles, only LED2 would be activated to illuminate the target spot 60. In yet another embodiment, a single light source could be used in conjunction with an electronic shutter, a liquid crystal shutter for example. During alternate master clock cycles, the shutter would permit the entire device to be illuminated (e.g., target spot and background), and then only the target spot area, or perhaps the entire device except the target spot area.

In FIG. 5, waveforms C and D depict the light detected by PDA and PDB respectively. The amplitude of waveforms C and D will vary slowly over time and represent the intensity of reflected light seen by PDA and PDB, respectively. Because PDA and PDB are spaced-apart $\Theta=180°$, their average combined output signals (e.g., the average sum of waveform A and waveform B) will be substantially free of error due to the irregular topography of the device membrane surface 50.

Figure 6C:
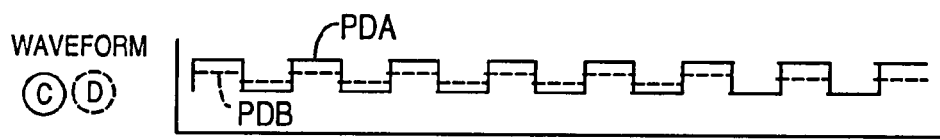
Figure 6D:
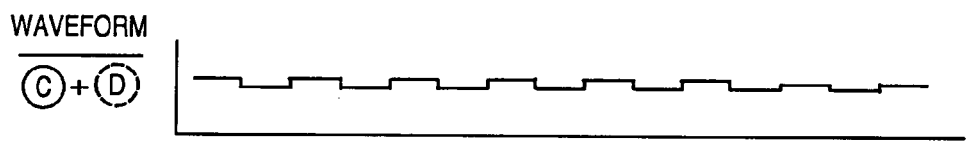
Figure 6E:
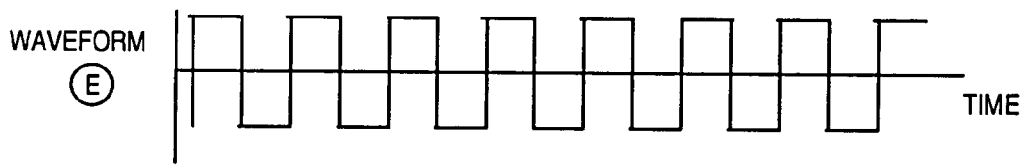

FIG. 6C depicts superimposed waveforms C and D. In the example shown in FIG. 6C, PDA sees more light reflected from the background region 70 and less light reflected from spot 60 than does PDB. Thus, the first cycle of FIG. 6C (when the drive signal to LED1 and LED3 shown in FIG. 6A is active or high) shows a large signal amplitude for PDA than for PDB, whose waveform is shown with phantom lines for clarity. During the next cycle of FIG. 6C (e.g., when LED2 is active, as shown by waveform B in FIG. 6B), the signal amplitude from PDB is higher than the signal amplitude from PDA, which means PDB sees more light reflected from the spot 60 than does PDA.

FIG. 6D shows the average of the two PD output signals. If signals were examined directly at the PD outputs, there would be an average steady-state level of perhaps 1 μA, with perhaps 1 μA peak-peak superimposed, in the presence of much reflected light, and with essentially no peak-peak superimposed signal in the absence of reflected light.

Summing amplifier 220 outputs the amplified average combined PD signals (e.g., the signals shown in FIG. 6D). These amplified signals are preferably AC-coupled by capacitor C1 and appear as waveform E, shown in FIG. 6E. Amplifier 220 provides substantially all of the gain for system 100, and has its output AC-coupled via capacitor C1 to eliminate offset voltage errors within sub-system 200. Of course offset voltages could be eliminated by replacing capacitor C1 with a bandpass filter, which could also eliminate noise in frequency ranges above and below the master clock switching frequency.

In 6E, waveform E may be as large as 20 V peak-peak for light reflected from a white background region; and will be essentially 0 V peak-peak in the absence of a spot, e.g., in the absence of any intensity contrast between the surrounding region and the region whereat a spot should be present.

Sub-system 210 receives the AC-coupled output (or bandpass-coupled output) from sub-system 200. Sub-system 210 includes positive and negative identical gain amplifiers 230, 240 that each receive waveform C as input, and that output, respectively, waveform D (a version of waveform C), and waveform E, an inverted version of waveform C. Waveforms D and E, shown in FIGS. D and E respectively, are thus phase-shifted relative to each other by 180° because of the inversion created by amplifier 240. In the preferred embodiment, amplifiers 230, 240 provide identical voltage gain, and can output about ±12 V maximum peak-peak output waveforms D and E to maximize signal/noise ratio. Signal to noise is enhanced because electronic noise (shot noise, random noise, etc.) does not increase with increasing power supply voltages, whereas output signals do increase in magnitude with increasing power supply voltages. Dominant noise sources in system 10 are photodetectors PDA, PDB, and to a lesser degree amplifier 220.

Figure 6F:
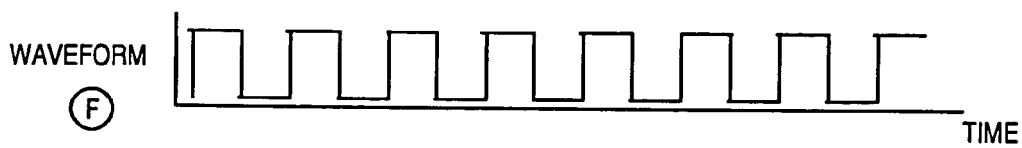
Figure 6G:
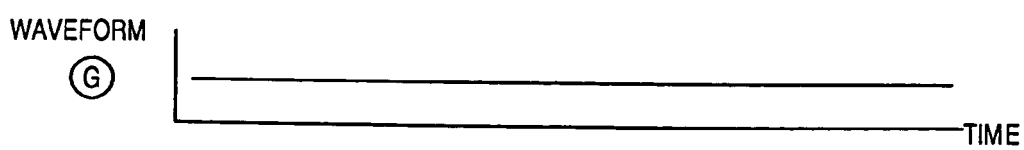

A switch 250 samples waveform signals D and E and produces a sampled waveform F, shown as FIG. 6F. Waveform F is then lowpass filtered (filter 260) to remove the high frequency sampling rate (here 2 KHz). The output of filter 260, waveform G shown as FIG. 6G, is a DC voltage proportional to relative signal/noise, which is to say, proportional to intensity of the colored spot. The DC waveform signal G may be digitized to produce a digital output, e.g., indicator 130, and/or an analog output, e.g., indicator 140. Circuitry 160 also includes a master clock 270 and LED drivers 280. A power supply 290 provides preferably ±12V operating potential to system 100. Power supply 290 may be provided from rectified 110/220 VAC in conventional fashion.

Alternatively, low voltage battery operation is also possible, for example using voltage doublers and voltage inverters, such as the commercially available Harris ICL7660 IC, to provide the desired supply voltages. Although such voltage doublers and inverts normally introduce ripple into the higher voltage level, the doubler-inverter clock circuit may be synchronized (or derived) from master clock circuit 270 in the present invention. If such synchronization is implemented, signal errors due to voltage multiplication ripple will be eliminated by system 210 and will not degrade or otherwise affect system 100 data readings.

Master clock 270 outputs a clock signal to conventional LED driver unit 280 causing LEDs LED1, LED2, LED3 to be active at about 2 KHz with a duty cycle of about 50%, although other drive frequencies and duty cycles could be used. Photodetectors PDA and PDB each receive at least a fraction of light output by an LED, and will themselves output a 2 KHz signal of varying amplitude, as shown in FIGS. 6A and 6B.

As noted, the input signal to sub-system 210 is AC-coupled, and thus has no DC offset. The peak-peak magnitude of waveform C may be as large as 20 V (i.e., ±10 V) for a very dark spot, and will be perhaps 0.2 V or less for a borderline specimen.

In general terms, a pure white colored membrane would generate a signal of about 3 μW of light on a photodiode detector having perhaps 5.2 mm² active area. This detected light output produces an electrical signal of about 1 μA that is input to a transconductance amplifier (e.g., amplifier 220), to generate an output voltage of about 1 V, which is then further amplified.

In practice, the present invention can readily resolve differences in reflectivity between spot 60 and the surrounding area 70 on device 10 of about 20 mV peak-peak, if not better. Note that a 1% error in measured reflectivity in FIG. 3B would generate a 200 mV peak-peak error at the input to sub-system 210, e.g., 1%×20V peak-peak. It will be appreciated that in a borderline analysis case, the difference between a positive analysis and a negative analysis can be determined by a detected light intensity difference of perhaps 20 mV to 30 mV or less.

Amplifiers 230, 240 in sub-system 210 perform as a lockin system. As noted, thus far signals A, B, C, D, E all are switched at the basic clock rate, e.g., about 2 KHz. However, from the output of switch 250 and continuing to lowpass filter 260, the relevant signals are now DC. It is the function of sub-system 210 to output a DC signal G that is proportional to light intensity received by PDA and PDB, without amplifying noise.

Switch 250 is operated in synchronism with master clock 270 and thus samples at the clock frequency, here 2 KHz. As such, frequency components other than 2 KHz do not get sample and thus do not contribute to the magnitude of waveform F. Noise components at say, 1 KHz or 3 KHz, for example are cancelled out by amplifiers 230 and 240, and do not contribute to waveform F or waveform G. The sampled waveform F signals are then input to low pass filter 260, which preferably is at least a two-pole filter with a zero located at the master clock frequency. Typically filter 260 exhibits a 3 dB roll-off frequency of about 20 Hz.

Lower frequency noise components, e.g., 60 Hz, is simply too slow to be seen by switch 250. For example, assume that there is a 100 Hz lower frequency noise component present in system 100. The 100 Hz waveform is sampled by PDA, PDB at 2 KHz (e.g., the master clock rate), and is amplified with gain +K (by amplifier 230) and by gain −K (by amplifier 240). Switch 250 then rapidly synchronously samples the signal portion of these opposite phase low frequency noise components.

In essence, sub-system 210 components 230, 240, 250 convert the 100 Hz noise signal to a 1900 Hz and 2100 Hz output signal. However these 1900 Hz and 2100 Hz components are substantially attenuated by 20 Hz lowpass filter 260, and thus the 100 Hz noise components does contribute to output signal G from system 100.

Thus, to pass a non-zero signal through lowpass filter 260, the signal must itself be sampled at the master clock frequency (here, 2 KHz) and must be synchronously in phase with the active portion of the master clock 270.

The active portion of the master clock signal will be the portion of the duty cycle that drives LED1, LED2, LED3, as switch 250 is synchronized to this portion of the master clock waveform. The only noise components allowed to pass through lowpass filter 260 will be components extremely close to the clock sampling rate of 2 KHz. Thus noise falling within the frequency spread of 2 KHz ±3 Hz may pass lowpass filter 260, but all other noise components will be substantially attenuated by the filter.

Consider the advantages provided by lock-in sub-system 210 with respect to improving system 100 signal/noise ratio. At the chosen master clock frequency (about 2 KHz), the noise contribution from the photodiode detectors PDA and PDB, and from summing amplifier 220 is about 0.08 $\mu V/Hz^{1/2}$. With a 20 Hz cut-off frequency lowpass filter 260, total output noise (waveform G) will be about $0.08*(20)^{1/2} \approx 0.4$ μV. The unfiltered output noise from the same photodiode-pair and amplifier would be about 1 mV. Thus, sub-system 210 reduces system noise by a factor of about 2,500, e.g., 1 mV/0.4 μV.

The synchronous phase detection provided by lock-in amplifiers 230, 240, switch 250 and lowpass filter 260 effectively double system signal/noise, as contrasted with a non-synchronous detector or narrowband filter having the same bandwidth. The enhanced signal/noise characteristics provided by sub-system 210, together with the topography cancellation feature provided by sub-system 200 enable system 100 to output reliable data with an accuracy that is substantially superior to what is available from prior art systems.

At a minimum accuracy is enhanced by at least ±1% due to inclusion of sub-system 200. As a result, for faint (low density) spots, system 100 can provide output information at indicator 130, 140 that can be relied upon. Under such circumstances, prior art systems would exhibit an error that is approximate in magnitude to the data being measured. Whereas prior art systems would be prone to provide false positive or false negative output, the present invention can provide true output information.

The use of system 100 in actually obtaining reflectivity information from a specimen on a device will now be described. In practice, device 10 will have been exposed to an analyte, chemicals, and will have been washed to produce a dyed spot 60 whose color density can contain meaningful information about the absence or presence of the analyte, as well as relative magnitude of the analyte. Alternatively, for purposes of the present invention, device 10 is presented to system 100, which will be used to discern intensity of the dyed spot 60 relative to surrounding membrane regions 70. In short, how spot 60 was generated on a surrounding region 70 is relatively unimportant to the present invention, providing the nominal spot diameter is appropriate to system 100.

Figure 1C:
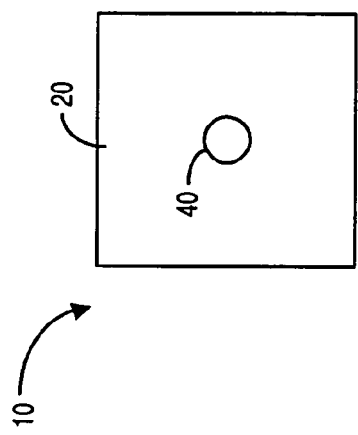
FIG. 1C is a plan view of the device of FIG. 1A depicting a fully formed dark spot.
Figure 1B:
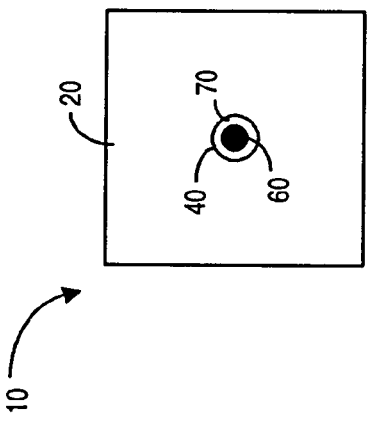
FIG. 1B is a plan view of the device of FIG. 1A, with no spot present.
Figure 1A:
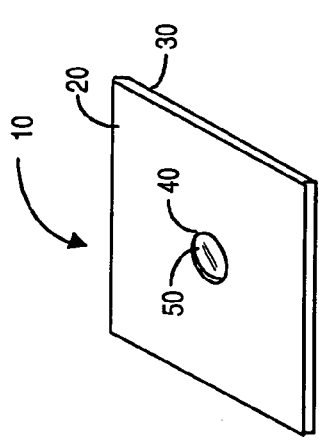
FIG. 1A is a perspective view of a spot-generating device with which the present invention may be practiced.
Figure 1F:
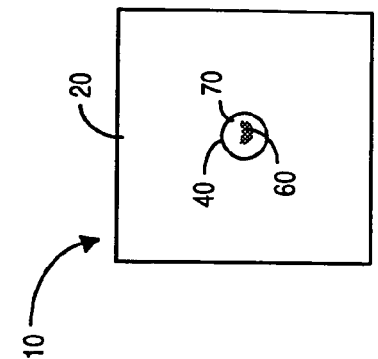
FIG. 1F is a plan view of the device of FIG. 1A depicting a misshaped lightly colored spot.
Figure 1E:
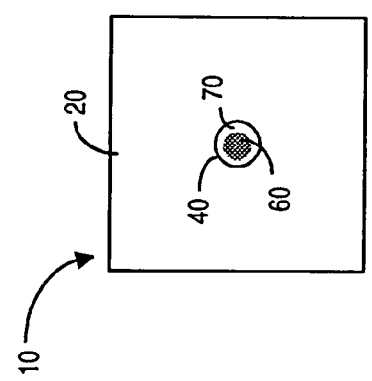
FIG. 1E is a plan view of the device of FIG. 1A depicting a fully formed lightly colored spot.
Figure 1D:
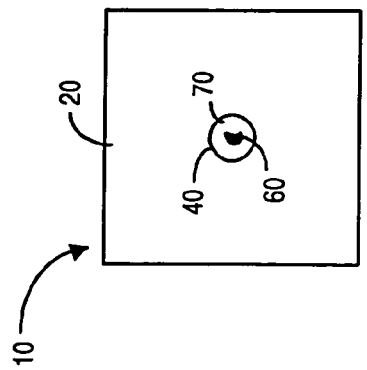
FIG. 1D is a plan view of the device of FIG. 1A depicting a misshaped dark spot.

Initially an undyed device 10, such as shown in FIG. 1B, will be inserted into holder 110, and a control, e.g., 150, will be adjusted to produce a zero readout on indicator 130 and/or 140. Alternatively, system 100 can include electronics to automatically zero the system when presented with a blank, preferably all white, device 10. The zero adjustment (manual or automatic) will essentially calibrate or set the background reference signal for a preferably white background. This calibrated signal level should then be obtained from regions 70 when using a device 10 containing a (preferably red) dyed spot 60 surrounded by regions 70.

The blank device is removed from holder 110, and a device containing an actual dyed specimen spot is inserted into the holder, e.g., a device such as shown in FIG. 1A, 1C–1F, without limitation. In practice, digital readout device 130 and/or analog readout device 140 will automatically indicate a reading within a second or so. The rapidity with which an output reading may be made is determined in part by the roll-off characteristics of lowpass filter 260.

The output reading will be a good measure of the intensity of the dyed spot relative to the undyed surrounding regions subjected to light from the present invention. Most significantly, system 100 can be operated by a layman, and the results can be copied down or stored electronically by optional memory within system 100, if desired.

It will be appreciated that output indicators 130, 140 can be customized to the task at hand. For example, a control 160 may be switchable to one of several positions such as "blood sample", "urine sample", which positions will cause output indicators 130, 140 to be re-normalized to the task at hand. By re-normalize, it is meant that output levels on indicators 130, 140 are re-scaled or recalibrated for the task at hand. For a blood specimen, perhaps a minimum digital reading of "12.3" is good, but for urine the minimum reading would be "9.6". Re-normalization could result in a proper reading for each specimen.

Once re-normalized, the output indicators can, if desired, indicate one of a number of outcomes based upon the measured light intensity data, for example: "good", "bad", "questionable". If desired, a digital output 130 could spell-out such words using an alphanumeric readout.

If desired, the shape of device 10 could be dedicated to different tasks. For example, if the specimen is blood, the upper righthand corner of device 10 could be clipped off; if the specimen is urine, the upper lefthand corner could be clipped off, etc. A microswitch or the like associated with holder 110 could then automatically sense what sort of data is to be presented, and could automatically re-normalize output indicators 130, 140. In any event, it will be appreciated that an untrained layman can successfully operate device 100.

System 100 can be manufactured in quantity for under $250 and can be fabricated is a form factor of perhaps 6 cm×15 cm×18 cm, or smaller. The ease of use, robustness, small cost and small size are all in sharp contrast to prior art systems. Further, the ability to compensate for membrane topography adds a minimum of 1% and up to perhaps 100% or more accuracy to the system readout, and the ability to measure peak signal without producing noise further enhances system reliability. The present invention obtains the maximum amount of optical information from the dyed spot than can prior art systems, and does so with increased accuracy and reliability.

The configurations shown in FIGS. 2–5 and waveforms 6A–6G are but illustrative of one embodiment of the present invention. Other embodiments providing topography correction and signal/noise enhancement are also possible. As was described, the embodiment of FIG. 4A seeks to minimize differential LED drift by using substantially identical LEDs. A different approach is taken in the embodiment of FIG. 7A, in which a single light source LS1 is used. Understandably, if the spot and surrounding regions, respectively 60, 70, can be illuminated from a single substantially uniform output light source, there will be no differential drift due to different light sources.

Thus, in FIG. 7A, a reflector unit 300 having an inner surface 310 that may be diffusive (perhaps white) or reflective (perhaps mirrored) directs rays from a single light source LS1 uniformly toward device 10. LS1 may be a LED or (if switching speed is less critical) incandescent, among other light sources. By providing a single light source whose light output preferably is well diffused before being directed to device 10, light source-to-light source variations that may be present in the multi-LED embodiment of FIG. 4A are eliminated.

Preferably the light rays from LS1 directed toward device 10 are non-focussed rays. If a diffusive non-focussed light is desired, a diffuser unit 320 may be included, and the inner surface 310 of unit 300 may itself be diffuse, e.g., perhaps a white surface. Alternatively, inner reflector surface 310 may be highly reflective, e.g., mirrored. Whether diffusive, reflective, or some combination thereof, inner surface 310 of reflector 300 may have various shapes, including without limitation, hemispheric and parabolic.

Perforated disk 340 defines through openings 370 through which light intended to illuminate background regions 70 may pass. Disk 340 also defines through openings 380 (shown in FIG. 7B) through which light intended to illuminate spot 60 may pass. In the preferred embodiment, circular disk 340 has eight openings 370 and four openings 380, a total of twelve openings in all.

In FIG. 7A, disk 340 is shown mounted at the first or light source plane. If desired, a rotatable disk 340 could instead be mounted adjacent the second plane or PD plane. This alternative embodiment is shown in FIG. 7A by a phantom disk 340'. Understandably, the location of the various through openings in a disk 340' mounted at the second plane will differ from the location of openings in a disk mounted at the first plane. For ease of illustration FIG. 7B does not include reflector unit 300.

Whether mounted at the first or second plane, perforated circular disk 340 is rotated by a motor 350 about a central disk spindle axis 360 under command of signals from master clock unit 270. Mechanical rotational speed (indicated as ω in FIG. 7B) is preferably at a frequency that will reduce system electronic noise, e.g., perhaps 100 Hz to about 5 Khz. Mechanical disk rotation permits light to strike or not strike the desired spot 60 or surrounding regions 70 on device 10. PD measurements are made when the desired openings are in an aligned position over device 10. Thus, background PD intensity readings from region 70 would be taken when a pair of openings 370 are aligned with device 10, as determined by signals from the master clock unit, which controls shutter movement. Similarly, spot PD intensity readings are taken when a single opening 380 is aligned over the spot area (again, as determined by signals from the master clock unit). Since disk rotation is controlled by master clock 270, output signals from PDA, PDB (which preferably have the same topography correcting azimuthal 90° or 180° orientation as in FIG. 4A, 4B) are similar to waveforms C and D in FIG. 5.

As was the case with FIG. 4A, different combinations of light illumination are possible. One combination is simply to alternately illuminate the spot 60, the surrounding regions 70, spot 60, surrounding regions 70, and so on. In FIG. 7A, the hole pattern in disk 340 will affect the lighting pattern. Alternatively, in FIG. 4A or in FIG. 7A, one can illuminate both spot and surrounding regions, and then illuminate either the spot alone, or the surrounding area (but not the spot). The PDA, PDB signals (corresponding to total illumination less spot alone or less surrounding area but not spot) can be subtracted to provide the desired signals for spot and background or surrounding regions.

Figure 7D:
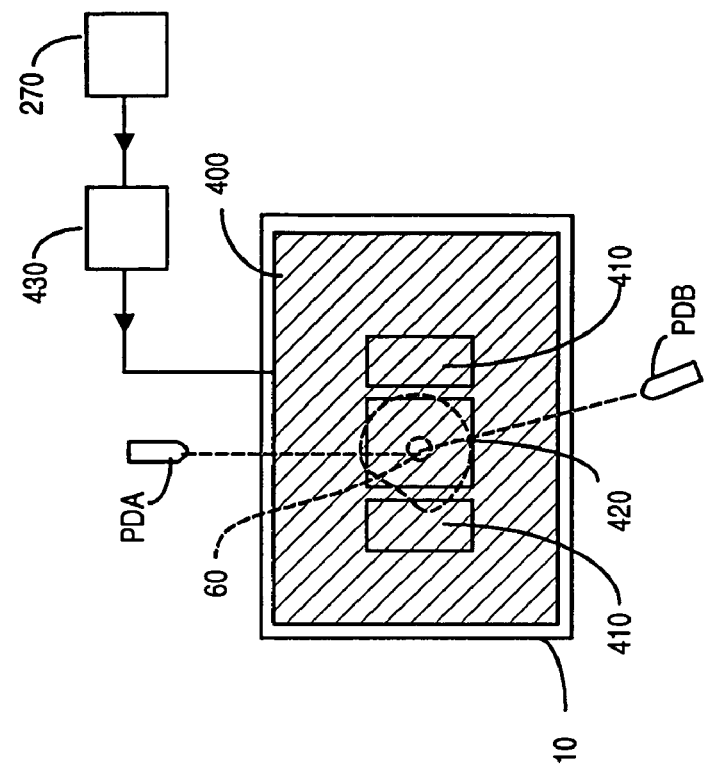
FIG. 7D is a simplified plan view of the configuration shown in FIG. 7C, according to the present invention.
Figure 7C:
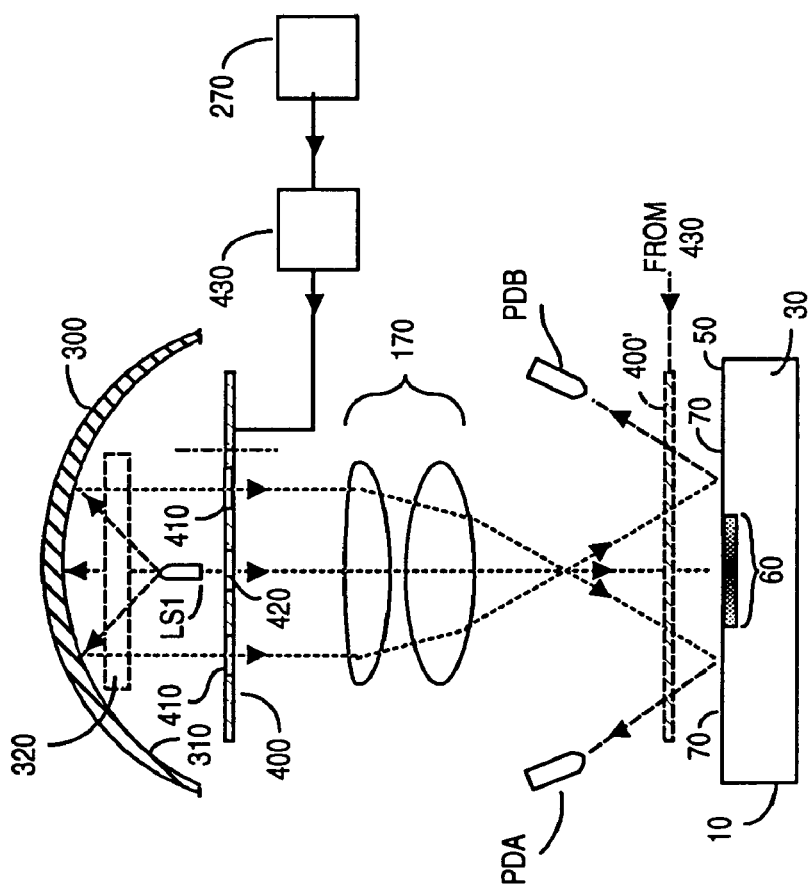
FIG. 7C is a side view of yet another embodiment in which a single light source and an electronic shutter are used to minimize skew due to membrane topography, according to the present invention.

The embodiment of FIG. 7D is somewhat analogous to FIG. 7A except that a preferably solid state (e.g., liquid crystal) shutter 400 is used instead of a mechanical shutter. Again, a single light source LS1 may be used with a reflector unit 300, preferably was described with respect to FIG. 7A. Uniformly distributed light from LS1 is to spot 60 or to surrounding regions 70 (or to spot 60 and regions 70, if desired) by selective passage through regions 410, 420 of shutter 400 that are selectively made transparent rather than opaque. Regions 410, 420 are changed from an opaque or reflective mode to a transparent mode by suitable electronic signals from a shutter driver 430 that responds to timing signals from master clock unit 270. As shown in phantom in FIG. 7C, a liquid crystal shutter 400' may be disposed at the second, PD, plane rather than at the first, LED, plane. For ease of illustration, FIG. 7D omits reflector unit 300.

Figure 7F:
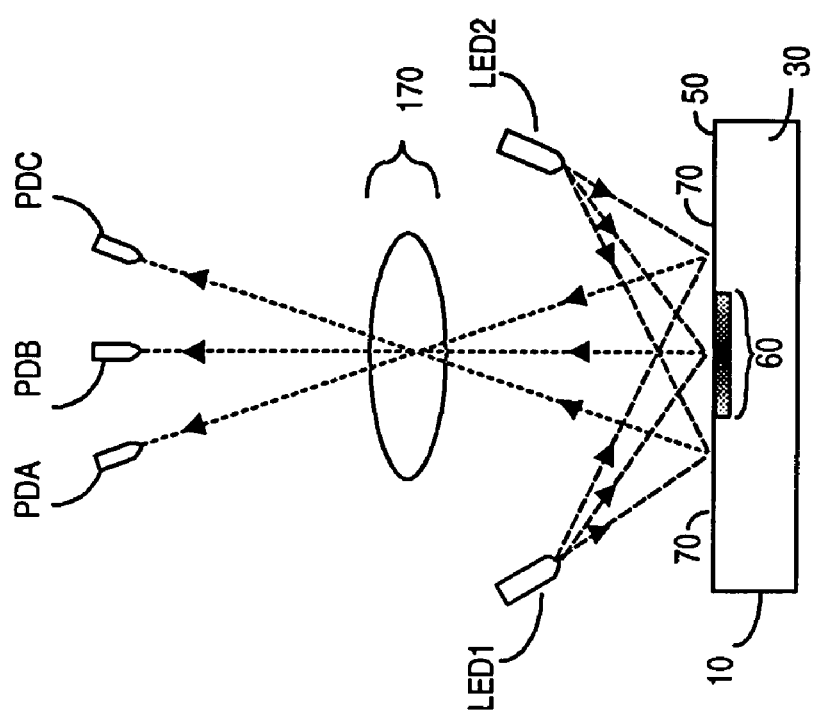
FIG. 7F is a side view of yet another embodiment in which the positions of LEDs and PDs are interchanged to minimize skew due to membrane topography, according to the present invention.
Figure 7E:
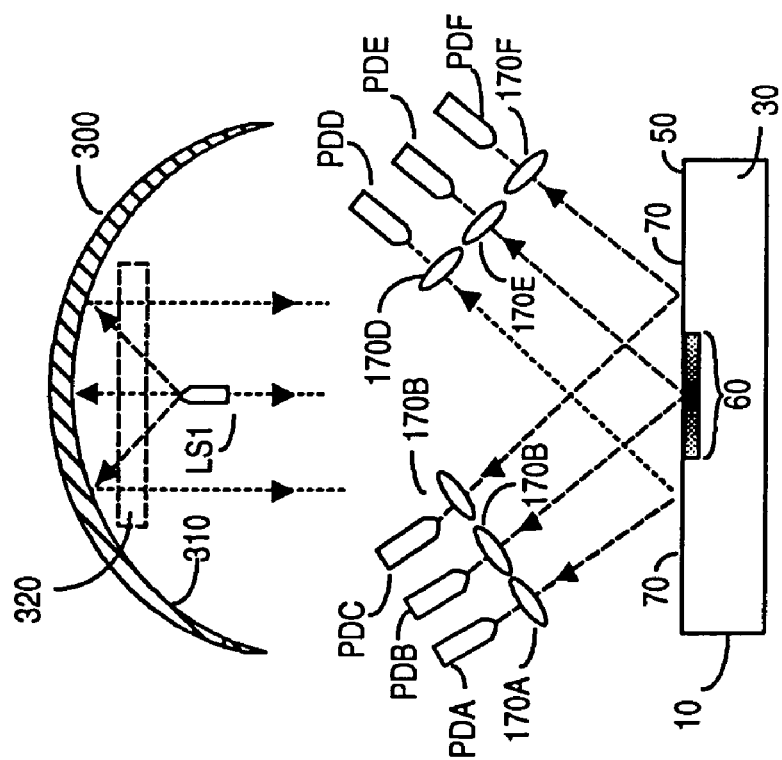
FIG. 7E is a side view of another embodiment in which a single light source and a plurality of focussed PDs are used to minimize skew due to membrane topography, according to the present invention.

FIG. 7E depicts an embodiment of the present invention in which a single light source LS1 in conjunction with reflector unit 300 (which may be identical to unit 300 as earlier described) illuminates device 10 via a lens system 170. In this embodiment, LS1 may be on at all times, although it may be pulsed on to conserve power supply consumption.

A plurality of PDs, her six preferably identical detectors PDA, PDB, . . . PDF, are disposed 90° or 180° azimuthally (depending on the grain nature of the membrane surface) as shown. Each PD has its own lens, e.g., lens 170A for PDA, lens 170B for PDB, etc. such that PDA and PDD, and PDC and PDF measure light from respective background regions 70, while PDB and PDE measure light from the spot area 60. It is understood that preferably the PDs are disposed three-dimensionally rather than planarly, and provide topography correction as earlier noted.

In the embodiment of FIG. 7E, LS1 can illuminate regions 70 and region 60 at all times. However the focussed nature of the various PDs ensures that the output from PDB and PDE will be a measure of spot intensity, whereas the output from the remaining PDs will be a measure of background area intensity. The outputs of the various PDs may be sampled, e.g., under control of a master clock unit if desired, such that it is known what signals represent what regions of the membrane surface of device 10. Signal processing may then occur similarly to what has been earlier described herein.

The embodiment of FIG. 7F reverses the positions of the LED focal plane and the PD focal plane: the LEDs are azimuthally inclined 90° or 180° close to device 10 (to minimize topography skew effects) and the PDs are disposed farther from device 10. While FIG. 7F shows two LEDs, LED1 and LED2, in practice additional LEDs, distributed three-dimensionally, may be used. Thus, if four LEDs were employed, in a plan view, LED1 and LED2 might be at 9:00 and 3:00 clock positions, with LED3 and LED4 are 12:00 and 6:00 clock positions. However, azimuthally, all LEDs would be inclined 90° or 180°, as dictated by the grain of the membrane surface.

FIG. 7F is somewhat analogous to FIG. 7E. In FIG. 7F, the membrane surface is substantially uniformly illuminated by the LEDs, and each PD is focussed upon a separate region of device 10. Thus, signals from PDB will be responsive to intensity of spot 60, whereas signals from PDA and PDC will be responsive to intensity of background regions 70. In FIG. 7F, master clock unit 270 and LED drivers 280 (see FIG. 5) preferably pulse the LEDs on and off. When the LEDs off, e.g., not activated, output signals from PDA, PDB, PDC are so-called zero signal drift errors (e.g., error signals from the amplified PDs in the absence of light). When the LEDs are on, signals from PDA, PDB, PDC will be responsive to reflected light. Subtracting the LEDs-off and the LEDs-on PD outputs will cancel the zero signal drift error components. Further processing of the signals may be carried out as has previously been described with respect to FIG. 5.

It will be appreciated that the present invention may be used in a wide spectrum of applications, biological and non-biological. For example, the devices disclosed in applicant Chu's pending U.S. patent application Ser. No. 08/823,936, filed Mar. 25, 1997, entitled ANALYTIC ASSAY DEVICE, incorporated herein by reference, may be used for immunoassays. The results of such immunoassays may be obtained using the present invention. Of course the range of detectable targets is not limited to analytes per se. Contaminants in the atmosphere, germs used in weaponry, among other substances may produce a spot, dyed or undyed, whose contrast relative to a pristine portion of a membrane is detectable with the present invention. Further, while the present invention has been described with respect to use of reflected, diffused, or otherwise directed visible light, it is understood that non-visible light may be used as well, for example, infra-red, ultra-violet, X-ray frequency radiation, or perhaps low energy laser light.

Modifications and variations may be made to the disclosed embodiments without departing from the subject and spirit of the invention as defined by the following claims.

What is claimed is:

1. A method of quantifying data to determine possible presence of a target analyte in a specimen in which a sample of said target analyte is placed upon a membrane having a spot region that, in the presence of said target analyte, changes at least one optical characteristic relative to surrounding regions of said membrane, the method comprising the following steps:

(a) alternately and periodically illuminating said surrounding regions of said membrane and said spot region with light from a light source, said light traversing an air path undeflected by any planar optical element disposed between said light source and said membrane;

(b) detecting light reflected from said spot region and from said surround regions of said membrane with light detectors disposed so as to reduce skew error due to irregularities in topography of said membrane, reflected said light traversing an air path undeflected by any planar optical element disposed between said light detectors and said membrane;

(c) signal processing output from said light detectors to discern from optical characteristic information of said spot region relative to optical characteristic information of said surrounding regions of said membrane presence of said target analyte; and (d) providing an output signal commensurate with an output from said signal processing.

2. The method of claim 1, step (b) includes disposing said detectors spaced-apart from each other with an azimuthal angular offset selected from a group consisting of 90° and 180°.

3. The method of claim 1, wherein at step (c) said optical characteristic includes at least one characteristic selected from a group consisting of (i) color, (ii) color density, (iii) optical density, and (iv) relative contrast of reflected said light.

4. The method of claim 1, wherein at step (a) said light source includes at least one light source selected from a group consisting of (i) a source of visible light, (ii) a source of non-visible light, (iii) at least one LED, (iv) at least one laser diode, (v) a source of incandescent light, (vi) a source of X-rays, (vii) a source of ultra-violet, (viii) a source of infra-red, (ix) a source of diffuse light, (x) a source of non-diffuse light.

5. The method of claim 1, wherein step (a) includes at least one step selected from a group consisting of (i) illuminating said spot region with a circular light pattern and illuminating said surrounding regions with annular light patterns, (ii) illuminating said spot region with a circular light pattern and illuminating at least one of said surrounding regions with a circular light pattern, (iii) illuminating at least one of said spot region and said surrounding regions with a non-circular light pattern, (iv) illuminating using multiple light sources, (v) illuminating from a single light source, (vi) alternately and periodically illuminating with a frequency ranging from about 100 Hz to about 10 KHz, and (vii) alternately and periodically switching illumination from said spot region to said surrounding regions.

6. The method of claim 1, wherein:
step (a) includes illuminating at least one of said spot region and said surrounding regions with a circular light pattern, wherein said spot region and said surrounding regions lie on a first line; and
step (b) includes disposing said light detectors on a second line normal to said first line such that said spot region and said surrounding regions are each substantially equidistant from said light detectors.

7. The method of claim 1, wherein at step (a) said light source is a single source of light, and step (a) further includes alternately and periodically illuminating by selectively passing light from said light source through a component selected from a group consisting of (i) a rotatable disk defining through openings placed and sized to pass light directed to at least one chosen region of said membrane, (ii) an electronic shutter defining regions selectively made transparent to pass light directed to at least one chosen region of said membrane, and (iii) a liquid crystal shutter defining regions selectively made transparent to pass light directed to at least one chosen region of said membrane.

8. The method of claim 1, wherein signal processing at step (c) includes improving signal/noise ratio by subtracting measured light intensity from said spot region from measured light intensity of said surrounding regions.

9. The method of claim 1, wherein at step (d), said output signal includes at least one signal selected from a group consisting of (i) a representation of a ratio of measured reflected light from said spot region to measured reflected light from said surrounding regions, (ii) a representation of a ratio of measured reflected light from said surrounding portions to measured intensity of illumination of said surrounding portions, (iii) a ratio of ratios, a first ratio representing measured reflect light from said spot region relative to measured intensity of illumination of said portion, and a second ratio representing of measured reflected light from said surrounding portions relative to measured intensity of illumination of said surrounding portions, (iv) a visual signal, (v) a printed output, (vi) a digital computer-interface signal, (vii) an audible sound having at least one acoustic characteristic proportional to said output signal, and (viii) an audible enunciation of at least one word appropriate to said output signal.

10. The method of claim 1, further including at least two steps carried out synchronously with periodicity of illuminating in step (b) selected from a group consisting of:
(i) measuring intensity of light reflected by said spot region and measuring intensity of light reflected by said surrounding regions;
(ii) combining inverted and non-inverted signals representing measured light intensity reflected by said spot region and measured light intensity reflected by said surrounding regions; and
(iii) switchably sampling signals representing an inverted amplified version and a non-inverted amplified version of measured reflected light intensities.

11. The method of claim 1, wherein step (a) includes alternatively and periodically illuminating at a chosen frequency in a range of about 100 Hz to about 10 KHz.

12. The method of claim 1, further including, prior to providing said output signal, filtering at least one signal measured at step (b) to reduce frequency components resulting from said alternatively and periodically illuminating.

13. The method of claim 1, wherein said target analyte includes at least one analyte selected from a group consisting of (i) nucleic acids, (ii) antigens, (iii) antibodies, (iv) haptens, (v) hapten conjugates, (vi) macro-molecules, (vii) proteins, (viii) polymers, and (ix) chemicals.

14. The method of claim 1, wherein emitted said light traverses paths through air different from paths traversed by reflected said light.

15. A reflectometry system to measure intensity of a spot on a substrate relative to intensity of a surrounding area of said substrate, said spot being exposable to a target analyte, the system including:
a master clock unit outputting at least a periodic master clock signal having a clock frequency and duty cycle;
at least one light source, coupled to an output of said master clock unit, emitting light controllably directed at said spot and controllably directed at said surrounding area, emitted said light traveling substantially through air in a path undeflected by any planar optical element disposed between said light source and said substrate;
first and second spaced-apart light detectors to detect fractions of emitted said light reflected by said surrounding area and by said spot, said first and second detectors disposed so as to reduce skew errors from irregularities in topography of said substrate, reflected said light traveling to said detectors substantially through air in a path undeflected by any planar optical element disposed between said light source and said substrate;
circuitry, operatively synchronously with said master clock signal, to synchronously and complementarily sample and process output signals from said first and second light detectors, to provide data quantifying said target analyte.

16. The system of claim 15, wherein:
said circuitry further substantially reduces output signal responses from said first and second light detectors in absence of reflect light, and
said circuitry includes AC-coupling so as to reduce offset drift.

17. The system of claim 15, wherein said circuitry includes a lock-in amplifier system.

18. The system of claim 15, wherein said circuitry includes:
a summing amplifier coupled to amplify and process output signals from said first and second light detectors to yield an average summed signal;
a non-inverting amplifier and an inverting amplifier AC-coupled to receive as input said average summed signal;
a switch coupled to alternatively sample, synchronously with said master clock signal, an output of said non-inverting amplifier and an output of said inverting amplifier, such sampling occurring during a transition free interval of an active portion of said master clock signal duty cycle when which said light source actively emits light;
wherein an output of said switch includes an average component representing data quantifying presence of said target analyte.

19. The system of claim 15, wherein said at least one light source illuminates said substrate in at least one manner selected from a group consisting of (i) said spot and said surrounding area are alternately illuminated, (ii) said spot and said surrounding area are simultaneously illuminated, and (iii) only said spot is illuminated and alternatively said surrounding area but for said spot is illuminated.

20. The system of claim 15, wherein said at least one light source is selected from a group consisting of (i) a source of visible light, (ii) a source of non-visible light, (iii) at least one LED, (iv) a laser diode, (v) a source of incandescent light, (vi) a source of X-rays, (vii) a source of ultra-violet, (viii) a source of infra-red, (ix) a source of diffuse light, (x) a source of non-diffuse light.

21. The system of claim 15, wherein emitted said light traverses paths through said air different from paths traversed by reflected said light.

* * * * *